United States Patent [19]
Ellis

[11] Patent Number: 5,334,160
[45] Date of Patent: Aug. 2, 1994

[54] INTRAVASCULAR CATHETER WITH SLEEVE AND METHOD FOR USE THEREOF
[75] Inventor: Louis G. Ellis, Minneapolis, Minn.
[73] Assignee: Scimed Life Systems, Inc., Maple Grove, Minn.
[21] Appl. No.: 878,727
[22] Filed: May 4, 1992
[51] Int. Cl.5 .................... A61M 5/178; A61M 5/32; A61M 31/00; A61M 5/00
[52] U.S. Cl. .................... 604/167; 604/53; 604/163; 604/256; 128/657
[58] Field of Search ............. 604/53, 163, 164, 167, 604/256; 128/657-658

[56] References Cited

U.S. PATENT DOCUMENTS

| | | | |
|---|---|---|---|
| 2,893,395 | 7/1959 | Buck | 128/349 |
| 4,149,535 | 4/1979 | Volder | 128/214.4 |
| 4,252,122 | 2/1981 | Halversen | 604/164 |
| 4,349,023 | 9/1982 | Gross | 604/164 |
| 4,417,886 | 11/1983 | Frankhouser et al. | 604/164 |
| 4,473,067 | 9/1984 | Schiff | 128/1 |
| 4,525,157 | 6/1985 | Vaillancourt | 604/52 |
| 4,529,399 | 7/1985 | Grosheng et al. | 604/53 |
| 4,563,176 | 1/1986 | Gustavsson et al. | 604/163 |
| 4,646,742 | 3/1987 | Packard et al. | 128/344 |
| 4,655,746 | 4/1987 | Daniels et al. | 604/53 |
| 4,696,667 | 9/1987 | Masch | 604/53 |
| 4,723,550 | 2/0988 | Bales et al. | 128/344 |
| 4,726,374 | 2/1988 | Bales et al. | 128/344 |
| 4,763,667 | 8/1988 | Manzo | 604/164 |
| 4,771,777 | 9/1988 | Horzewski et al. | 604/101 |
| 4,838,269 | 6/1989 | Robinson et al. | 128/344 |
| 4,842,591 | 6/1989 | Luther | 604/283 |
| 4,844,092 | 7/1989 | Rydell et al. | 128/772 |
| 4,857,057 | 8/1989 | Sanagi | 604/164 |
| 4,875,480 | 10/1989 | Imbert | 604/53 |
| 4,929,243 | 5/1990 | Koch et al. | 604/283 |
| 4,932,413 | 6/1990 | Shockey et al. | 604/53 |
| 4,935,010 | 6/1990 | Cox et al. | 604/122 |
| 4,947,864 | 8/1990 | Shockey et al. | 128/772 |
| 5,009,391 | 4/1991 | Steigerwald | 251/149.1 |
| 5,040,548 | 8/1991 | Yock | 128/898 |
| 5,041,085 | 8/1991 | Osborne et al. | 604/51 |
| 5,045,061 | 9/1991 | Seifert et al. | 604/96 |
| 5,059,186 | 10/1991 | Yamamoto et al. | 604/280 |
| 5,061,273 | 10/1991 | Yock | 606/194 |
| 5,062,836 | 11/1991 | Wendell | 604/167 |
| 5,087,080 | 2/1992 | Shutt | 285/5 |
| 5,098,393 | 3/1992 | Amplatz et al. | 604/167 |
| 5,098,394 | 3/1992 | Luther | 604/167 |
| 5,100,386 | 3/1992 | Inoue | 604/103 |
| 5,102,395 | 4/1992 | Cheer et al. | 604/256 |
| 5,106,054 | 4/1992 | Mollenauer et al. | 251/149.1 |
| 5,114,403 | 5/1992 | Clarke et al. | 604/96 |
| 5,117,839 | 6/1992 | Dance | 128/772 |
| 5,120,299 | 6/1992 | Lombardi | 600/18 |
| 5,129,887 | 7/1992 | Euteneuer et al. | 606/194 |
| 5,137,513 | 8/1992 | McInnes et al. | 604/53 |
| 5,163,911 | 11/1992 | Sirimanne et al. | 604/164 |
| 5,195,980 | 3/1993 | Catlin | 604/167 |
| 5,203,774 | 4/1993 | Gilson et al. | 604/165 |

FOREIGN PATENT DOCUMENTS

| | | | |
|---|---|---|---|
| 1514019 | 6/1978 | European Pat. Off. | |
| 0250891 | 1/1988 | European Pat. Off. | 604/53 |
| 0267584 | 5/1988 | European Pat. Off. | |
| 0267584 | 5/1988 | European Pat. Off. | |
| 0314470 | 5/1989 | European Pat. Off. | 604/53 |
| 0440479A2 | 8/1991 | European Pat. Off. | |
| WO83/02065 | 6/1983 | PCT Int'l Appl. | |
| WO89/06986 | 8/1989 | PCT Int'l Appl. | |
| WO89/06986 | 8/1989 | PCT Int'l Appl. | |
| WO83/02065 | 6/2383 | PCT Int'l Appl. | |

OTHER PUBLICATIONS

Scimed, The Ace PTCA Dilatation Catheter Instructions for Use, Warranty and Limitations, Jan. 1990.

Primary Examiner—Randall L. Green
Assistant Examiner—Elizabeth M. Burke
Attorney, Agent, or Firm—Willian Brinks Hofer Gilson & Lione

[57] ABSTRACT

An improved intravascular catheter, such as a balloon catheter, and a method for use thereof. The catheter includes an elongate shaft and the improvement includes a close fitting sleeve located around the shaft and movable therealong. The intravascular catheter is adapted to be used with an introducer device, such as a guide catheter, having a hemostatic valve located at a proximal end thereof. The close fitting sleeve is adapted to be positioned at the hemostatic valve so that the hemostatic valve can be sealed upon the sleeve allowing the intravascular catheter shaft to be readily advanced in relation to the hemostatic valve and introducer device while limiting bleeding between the sleeve and the shaft of the intravascular catheter.

12 Claims, 2 Drawing Sheets

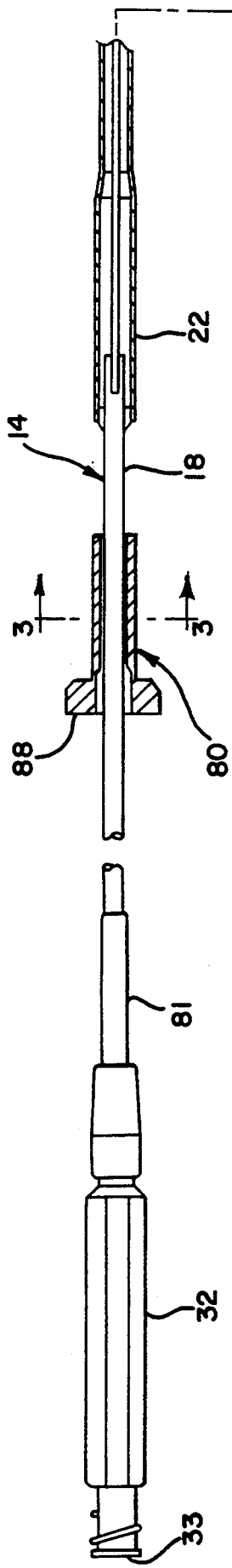
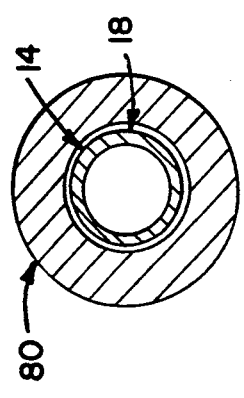
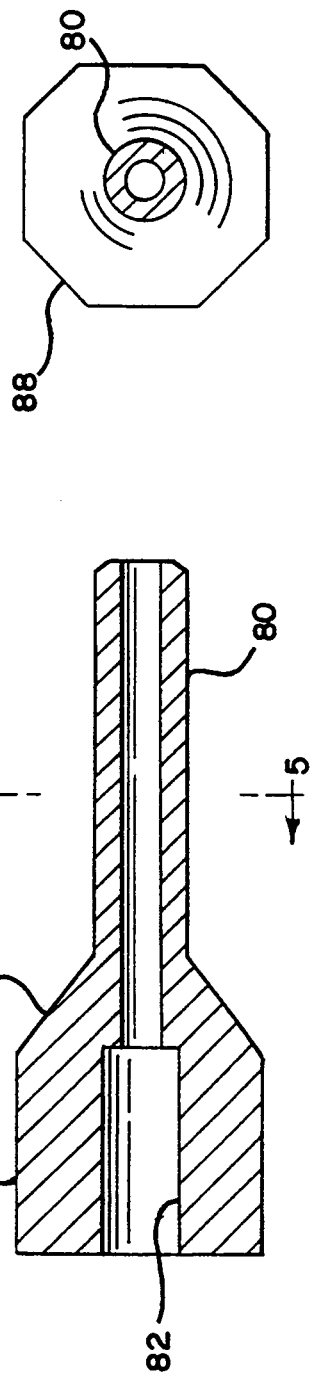
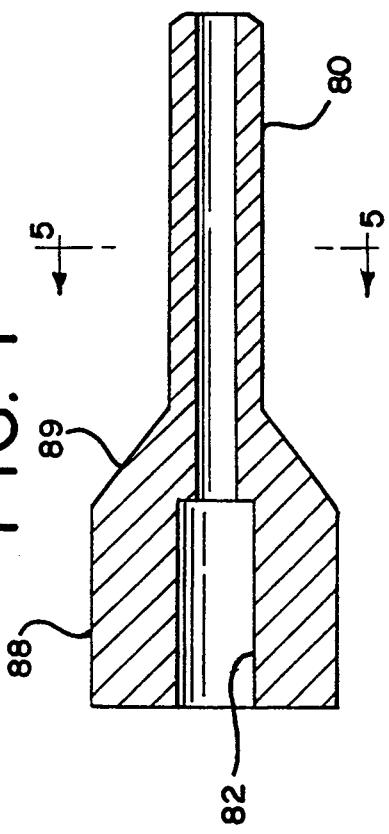
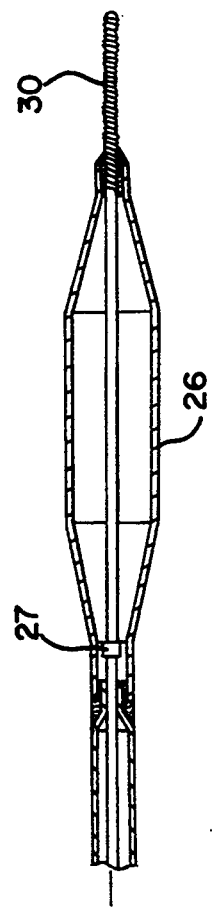

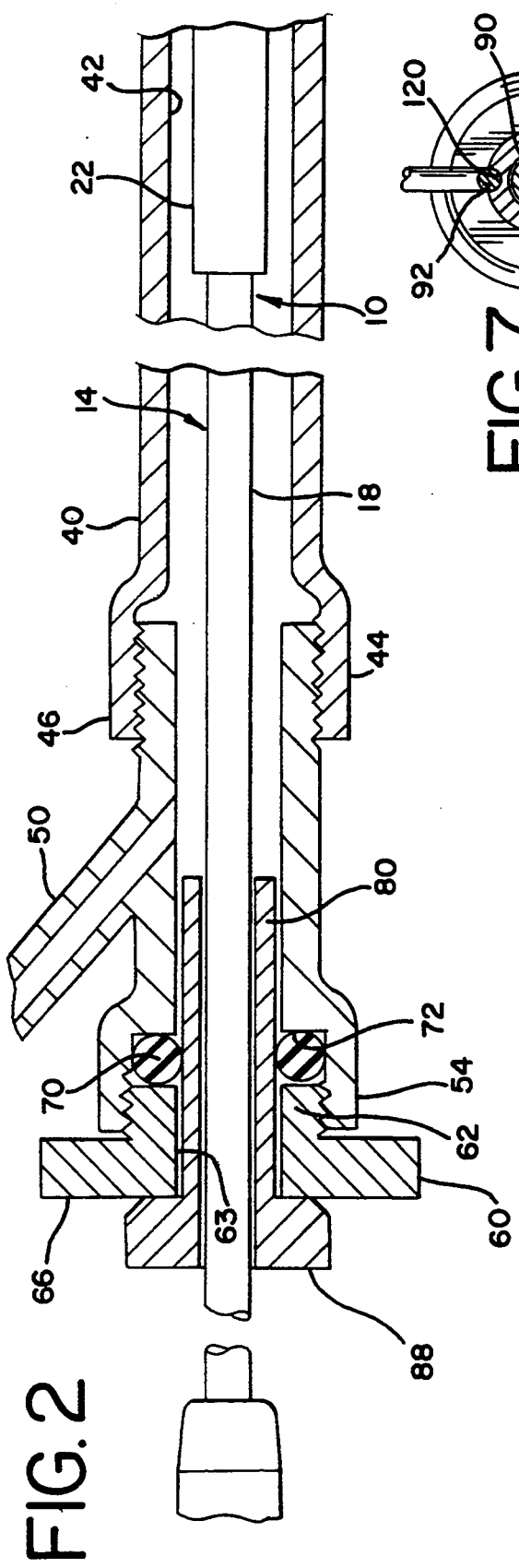
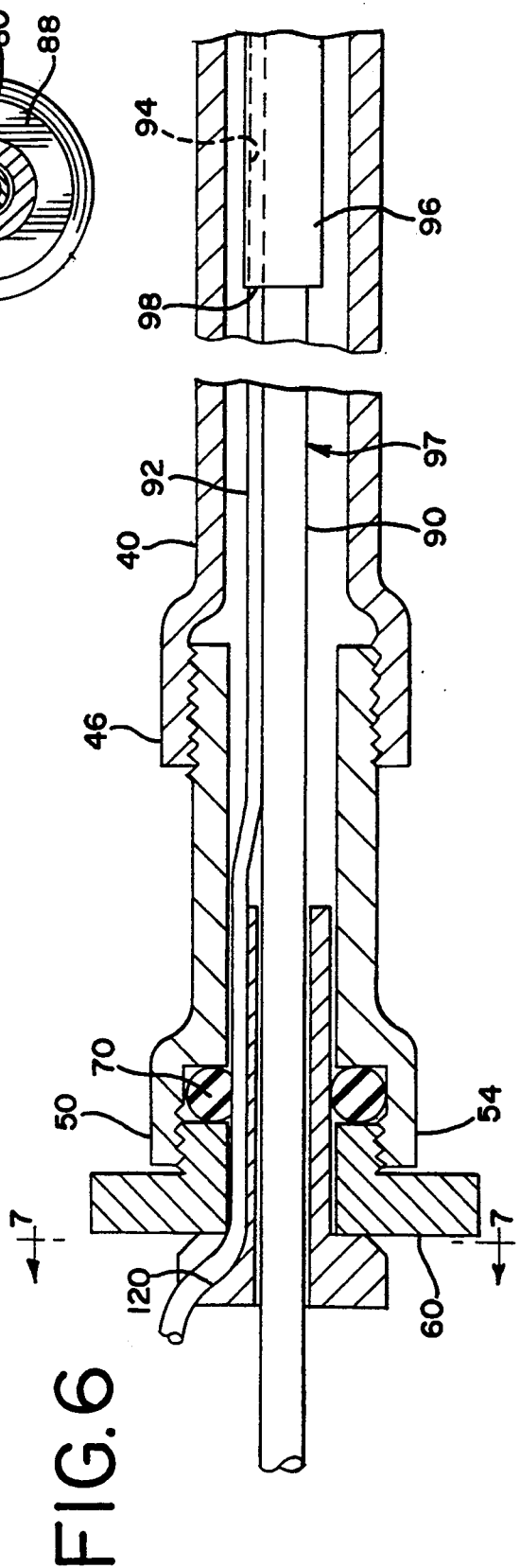

INTRAVASCULAR CATHETER WITH SLEEVE AND METHOD FOR USE THEREOF

BACKGROUND OF THE INVENTION

This invention relates to an improved intravascular catheter and methods for use thereof.

Intravascular catheterization apparatuses have proven to be useful and efficient for both therapeutic and diagnostic purposes. Intravascular catheterization therapies, such as angioplasty, atherectomy, and laser irradiation, have been developed as alternatives to by-pass surgery for treating vascular diseases or other conditions that occlude or reduce the lumen size of portions of a patient's vascular system. In particular, balloon angioplasty has proven to be a useful, and in many circumstances a preferred, treatment for obstructive coronary diseases. Also, intravascular diagnostic catheter apparatuses, for anglographics, ultrasonic imaging, and Doppler blood flow measurements for example, have been developed to measure or image the extent of an occlusion of a vessel, (e.g., stenosis).

These intravascular therapeutic and diagnostic catheter apparatuses have achieved acceptance because of their effectiveness as well as the fact that they can be used through a minor surgical procedure that is relatively non-disruptive to the patient compared to coronary surgery. These intravascular therapeutic and diagnostic apparatuses rely on the positioning of a catheter device into the vascular system of a patient via an incision at an accessible location which may be remote from the site of the occlusion or stenosis. For example, the accessible location may be the femoral artery at the groin. The intravascular device is then advanced through the incision via the femoral artery to the desired coronary distal site.

It is conventional in performing an intravascular coronary angioplasty procedure to use a guide catheter to support the balloon dilation catheter in the artery from the incision site to close to the coronary site. The guide catheter extends from outside the body to the ostium of the coronary vessel and provides a pathway via a lumen therein for the positioning of other intravascular apparatuses, such as the guide wire and the balloon catheter, through the artery to the coronary vessels. At the proximal end of the guide catheter there is a fitting, such as a luer lock, to which a manifold device such as a Y-adapter is connected. The dilation catheter is positioned through one of the ports of the Y-adapter (e.g. the axially oriented port) and into the guide catheter. This port of the Y-adapter through which the dilation catheter extends includes a hemostatic seal valve. The hemostatic seal valve includes a threaded knob that can be tightened down onto an O-ring seal located in a seat of the Y-adapter port. The hemostatic seal valve allows a physician to close the port when a dilation catheter is not in the guide catheter, or to seal the O-ring around the dilation catheter when it is in the guide catheter. Because the guide catheter provides a direct access to the artery, the hemostatic valve reduces or prevents bleeding from the artery both when a dilation catheter is in the artery and when a dilation catheter is not in the artery. Thus, the hemostatic seal valve located in a port of the Y-adapter facilitates intravascular procedures, such as angioplasty.

A difficulty sometimes encountered in the use of the hemostatic seal valve, as described, relates to adjusting the hemostatic valve to allow advancement of a balloon catheter while minimizing bleeding back through the valve. This difficulty is especially encountered when using a dilation catheter having a small diameter shaft. Catheters of this type include some fixed-wire type catheters and catheters having an opening to a proximal end of a guide wire lumen located in a distal portion of the shaft. A fixed-wire type catheter includes a non-removable wire tip located on the distal end of the dilation catheter. This wire tip is used for positioning the fixed-wire dilation catheter into the desired arterial site after it is advanced past the distal end of the guide catheter. The wire tip may be bent or formed with a J-configuration to facilitate steering it —and thus the dilation catheter— into the desired location.

The dilation catheter is handled and steered from the proximal end. During this steering and positioning, the physician attempts to adjust the hemostatic seal valve so that it is loose enough to allow unimpeded advancement and steering of the dilation catheter from the proximal end for the delicate positioning procedure. If the hemostatic valve is clamped down too tight on the dilation catheter, it can cause considerable friction with the catheter shaft that can impede advancing and steering of the dilation catheter. On the other hand, if the hemostatic valve is too loose, it allows bleeding back through the guide catheter and out the Y-adapter hemostatic valve which is undesirable and which can also impede handling of the equipment. Thus, the physician is presented with an unsatisfactory trade-off between minimizing blood loss and maximizing unimpeded catheter shaft movement. Moreover, adjustment the hemostatic valve to provide an tolerable balance of these considerations can be difficult or tedious and time-consuming during an interventional procedure. Therefore, there is a need for a improvement that facilitates intravascular procedures and facilitates advancement and steering of an intravascular catheter, such as balloon catheter, through a hemostatic valve of a Y-adapter while at the same time minimizing or reducing bleeding back through the guide catheter around the hemostatic valve.

SUMMARY OF THE INVENTION

According to the present invention there is provided an improved intravascular catheter, such as a balloon catheter, and a method for use thereof. The intravascular catheter includes an elongate shaft and the improvement includes a close-fitting sleeve located around the shaft and movable therealong. The intravascular catheter is adapted to be used with an introducer device, such as a guide catheter, having a hemostatic valve located at a proximal end thereof. The close fitting sleeve is adapted to be positioned at the hemostatic valve so that the hemostatic valve can be sealed upon the sleeve allowing the intravascular catheter shaft to be readily advanced in relation to the hemostatic valve and introducer device while limiting bleeding between the sleeve and the shaft of the intravascular catheter.

In a first aspect, the intravascular catheter is a dilation balloon catheter of the fixed-wire type. According to a second aspect, the intravascular catheter is a dilation balloon catheter of the type that uses a separate guide wire for positioning of the balloon and further which has a guide wire lumen located at the distal portion of the catheter with a proximal opening to the guide wire lumen located in a distal portion of the shaft.

BRIEF DESCRIPTION OF THE FIGURES

FIG. 1 is a side elevational view of a first preferred embodiment of a balloon dilation catheter of the present invention.

FIG. 2 is a sectional side elevational view showing a portion of the embodiment of a balloon dilation catheter shown in FIG. 1 positioning inside of a guide catheter and showing a hemostatic valve in a Y-adatper.

FIG. 3 shows a cross sectional view of a portion of the embodiment depicted in FIG. 1 taken along lines 3—3'.

FIG. 4 is a longitudinal sectional view of an embodiment of the sleeve of FIG. 1 shown apart from the balloon dilation catheter.

FIG. 5 is a cross sectional view of the embodiment the sleeve of FIG. 4 through line 5—5'.

FIG. 6 is a sectional side elevational view similar to that of FIG. 4 showing a portion of a second embodiment of a balloon dilation catheter.

FIG. 7 shows a cross sectional view of a portion of the embodiment depicted in FIG. 6 taken along lines 7—7'.

DETAILED DESCRIPTION OF THE PRESENTLY PREFERRED EMBODIMENTS

Embodiments of the present invention described herein are dilation balloon catheters for use in PTCA procedures. It should be understood that these embodiments may be adapted to other types of intravascular devices, such as atherectomy catheters, laser irradiation catheters, and diagnostic catheters such as ultrasonic catheters, anglographic catheters, and catheters used in other percuntaneous vascular procedures.

Referring to FIG. 1, there is depicted a PTCA balloon dilation catheter 10 according to a first embodiment of the present invention. The balloon dilation catheter 10 includes an elongate catheter shaft 14 formed of a tubular member having a proximal portion 18 and a distal portion 22. In a preferred embodiment, the proximal portion 18 is formed of a teflon-coated stainless steel and the distal portion 22 is formed of polyethelene.

A dilation balloon 26 is located at and connected to the distal portion 22 of the catheter shaft 14. The balloon 26 can be formed from a polymer material. For example, in one embodiment, the balloon 26 is formed of a polyolefin copolymer (such as that sold by DuPont under the tradename SURLYN as Resin No. 8527) using secondary treatment with 5 to 50 Mega-rad electron beam irradiation to enhance strength in the region of the balloon 26. The balloon 26 is provided in a variety of conventional sizes suitable for PTCA use. A marker 27 of a radiopaque material, such as a platinum alloy is bonded to the shaft 14 or a core wire extending therethrough in the region of the balloon 26.

Located at the distal end of the catheter shaft is a tip member 30. The tip member 30 is preferably formed of a coil spring located around a core wire. The coil spring is very flexible and can be bent or formed, e.g. into a J-shape, to facilitate positioning in the coronary arteries. The tip member 30 in this embodiment is bonded to the elongate shaft 14 and is non-removable. In a preferred embodiment, the coil spring may be made of a platinum alloy and the core wire of stainless steel.

Located at a proximal end of the shaft 14 is a manifold 32 having at port 33 communicating with an inflation lumen that extends through the shaft for inflating the balloon 26 in a conventional manner to dilate a vessel. In a preferred embodiment, the manifold 32 may be formed of a hard plastic, such as polycarbonate.

The dilation catheter 10 is positioned into the coronary vessels via a conventional guide catheter. Referring to FIG. 2, a guide catheter 40 has a lumen 42 extending therethrough and through which the dilation catheter 10 can be advanced from a proximal end 44 of the guide catheter 40 located outside the body of the patient to the ostium and coronary vessels at a distal end (not shown) of the guide catheter 40. Located at the proximal end 44 of the conventional guide catheter 40 is a proximal fitting 46. This fitting 46 is typically a luer lock. A conventional Y-dapter 50 is attached to the proximal fitting 46 of the guide catheter 40. The Y-adapter 50 has one or more ports to provide access to the guide catheter 40. In particular, the Y-adapter 50 has a port 54. The port 54 is axially aligned with the guide catheter lumen 42. The dilation catheter 10 extends through the port 54 of the Y-adapter 50. Although reference is made herein to a Y-adapter, it should be understood that the other types of devices may be connnected to or incorporated at the proximal end of the guide catheter or other insertion sheath device. Further, the Y-adapter may have more or fewer than two ports.

A hemostatic seal valve 60 is fitted in the port 54 of the Y-adapter 50. The hemostatic seal valve 60 includes a body 62 having a thread on the outer side adapted to engage an internal thread in the port 54 of the Y-adapter 50. The hemostatic seal valve body 62 has a cylindrical passageway 63 therethrough. The hemostatic seal valve 60 also has a handle portion 66 that the physician can use to rotate the hemostatic seal valve body 62. An O-ring 70 is located in a seat 72 of the Y-adapter 50. The dilation catheter 10 is located in the passageway 63 of the hemostatic seal valve body 62 and through the opening of the O-ring 70.

The body 62 of the hemostatic seal valve 60 is adapted to compress the O-ring 70 against the seat 72 when the valve body 62 is rotated clockwise. When compressed against the seat 72 by the valve body 62, the O-ring 70 deforms and bulges axially inward thereby reducing the size of the opening therethrough. In this manner, the hemostatic seal valve 60 can clamp down on the catheter 10 to prevent bleeding therearound through the guide catheter 40. The hemostatic seal valve 60 when tightened sufficiently can also fix the position of the balloon catheter 10 in the vascular site.

In the embodiment of FIGS. 2 and 3, a sleeve 80 is located around the catheter shaft 14. The sleeve 80 is located on the shaft 14 along the portion thereof distally of the manifold 32. If a strain relief member 81 is located on the shaft 14 immediately distally of manifold 32 (as shown in FIG. 1), the sleeve 80 is located distally of the strain relief 81. In a preferred embodiment, the sleeve 80 is adapted to releasably engage the strain relief 81 to fix it in position thereto until use, if desired. This feature may be provided by incorporation of a snap-fit rib on the strain relief 81 or the sleeve 80.

The sleeve 80 is sized and adapted to be slidable along the catheter shaft 14. Also, the sleeve 80 is adapted to be close-fitting on the shaft 14. In a preferred embodiment, the sleeve 80 is sized to provide a clearance of approximately 0.0007 inches between an inner surface of the sleeve 80 and the outer surface of the shaft 14. For example, with a catheter shaft having an outside maximum diameter of 0.025 inches (with a nominal O.D. of approximately 0.024 inches) the sleeve 80 has an inside diameter of 0.0257. With catheters having dimensions other than this, the size of the sleeve may be made accordingly different.

The sleeve 80 is preferably formed of a relatively rigid plastic material such as polyethelene. In a preferred embodiment, the sleeve 80 is approximately 50 mm in length and has in outer diameter of 0.060 inches and a inner diameter of 0.0257 inches. In order to accomodate releasably fitting onto the strain relief member 81 having a typical O.D. of 0.045 inches, a proximal portion 82, e.g. 10 mm, of the inner bore of the sleeve 80 has a diameter of 0.0540 inches.

In an alternative embodiment, it may be preferred to provide for a snap-fit connection between the sleeve 80 and the shaft 14. This may be provided by providing a projecting rib, for example on the strain relief member 81, that engages a depression on a corresponding area of the inner bore of the sleeve by an interference fit.

In some catheters, the distal portion 22 of the elongate shaft 14 has a somewhat larger diameter than the proximal portion 18. With this type of catheter construction, the sleeve 80 is movable along the proximal portion 18 of the catheter shaft 14, but not along the distal portion 22. This is because the sleeve 80 will be utilized when the dilation catheter 10 is advanced and the proximal portion of the dilation catheter is aligned with the hemostatic valve 60. If the distal portion 22 of the catheter shaft 14 is larger in diameter than the proximal portion 18, the sleeve 80 will be positioned around the proximal shaft portion 18 during the construction of the catheter 10 before either the manifold 32 or the distal portion 22 are connected to the proximal portion 18. Even if the distal portion 22 is not larger in diameter than the proximal portion 18, it would be preferred to position the sleeve 80 on the shaft 14 during construction of the catheter 10 to eliminate the possibility of damaging the balloon 26 by advancing the sleeve 80 over the balloon 26. Thus, in a preferred embodiment, the sleeve 80 is not removable from the shaft 14 although it can be slid along it.

Also, in a preferred embodiment, the sleeve 80 includes a proximal hub portion 88. Referring to FIGS. 4 and 5, the hub portion 88 is located at the proximal end of the sleeve 80. The hub portion 88 has a larger size, e.g. diameter of than the rest of the sleeve 80. The hub portion 88 facilitates handling of the sleeve 80 by the physician, e.g. sliding the sleeve 80 relative to the catheter shaft 14. Also, the hub portion 88 facilitates positioning of the sleeve 80 in the hemostatic valve and prevents the sleeve 80 from passing through the valve into the guide catheter. In a preferred embodiment, the hub portion 88 is formed of the same one piece plastic mold as the rest of the sleeve 80, although in alternative embodiments, the sleeve 80 and hub 89 could be formed of separate pieces connected together. The hub portion 88 has an outside diameter of approximately 0.40 inches and a length of approximately 10 mm. A tapering transition section 89 may be located extending from the distal end of the hub portion 88. In a preferred embodiment, the tapering section 89 is approximately 5 mm in length.

In operation, the physician or technician prepares the balloon catheter 10 and other equipment, such as the guide catheter and accessories, in the usual and conventional manner. The sleeve 80 is already positioned on the shaft 14 during the manufacture of the catheter 10, as mentioned above. The guide catheter 40 is positioned in the patient, also in the usual manner. The dilation catheter 10 is positioned through the port 54 of the Y-adapter 50 into the guide catheter 40. The dilation catheter 10 is advanced into the guide catheter 40 sufficiently so that the sleeve 80 can be positioned at the hemostatic valve 40 directly underneath the O-ring 70. The O-ring 70 is sufficiently tightened by rotation of the hemostatic valve handle 66 so that the O-ring 70 is tight upon the sleeve 80. When so tightened, the O-ring 70 prevents bleeding from between the O-ring 70 and the sleeve 80. The sleeve 80 is close-fitting to the catheter shaft 14 to reduce bleeding between the sleeve 80 and the shaft 14 yet is not so tight that it impedes ready advancement and movement of the shaft 14 when the O-ring 70 is tightened. After tightening of the O-ring 70 on the sleeve 80, the physician can continue to freely advance and steer the dilation catheter 10 to the arterial site in a conventional manner. After the dilation is completed, the dilation catheter 10 can be withdrawn, also in a conventional manner. The O-ring 70 can be loosened to allow the sleeve 80 to be withdrawn with the dilation catheter 10 from the guide catheter 40. Thus, with the use of this embodiment of the present invention, a dilation catheter of the fixed-wire type can be used with a conventional hemostatic seal valve 60 in a manner that facilitates use and adjustment of the valve to reduce back bleeding while allowing for advancement and steering of the catheter 10.

Referring to FIGS. 6 and 7, there is depicted another embodiment of the present invention. In FIGS. 6 and 7, an intravascular catheter 90 is of the type that uses a separate guide wire 92 for positioning, and specifically, the intravascular catheter is of the type that possesses a short guide wire lumen (SGWL) 94 located at the distal portion 96 of an elongate shaft 97 of the catheter 90. In this type of intravascular catheter, the separate guide wire extends through the dilation catheter 90 through a proximal guide wire lumen opening 98, the balloon portion (not shown), and a distal guide wire lumen opening located distal of the balloon. The proximal guide wire lumen opening 98 is located at a portion of the intravascular catheter normally located within the body during use. The proximal guide wire lumen opening 98 may be located close to the balloon or may be spaced away from the balloon, e.g. 5–40 cm. The proximal guide wire lumen opening 98 may be either in the guide catheter 40 or located distally thereof.

Proximal of the proximal guide wire lumen opening 98, the guide wire 92 is located adjacent to the catheter 90, e.g. within the guide catheter 40. This type of dilation catheter facilitates exchanges such as when it is required to exchange a first catheter for another catheter of a different size for example. With this type catheter design, the guide wire may be left in position in the arterial site while the first catheter is withdrawn and the second catheter can be advanced over the guide wire without the necessity for positioning the guide wire a second time.

When positioning the shorter-guide-wire-lumen catheter 90, according to one method of use, the guide wire is advanced and positioned into the arterial site first and then the dilation catheter is advanced over it. Also, for example, when performing a catheter exchange, the first catheter is withdrawn over the guide wire so that the guide wire is left in position in the desired arterial site. Then, the second dilation catheter is loaded over the proximal end of the guide wire and advanced over it to the desired arterial site. A concern with advancing or withdrawing a shorter-guide-wire-lumen catheter over a guide wire in this manner is that the movement of the catheter along the guide wire can dislodge it causing a loss of position or damage to the artery. Further, advancing a catheter over a guide wire in this manner requires carefully maintaining a tension on the guide wire while pushing the catheter over it. This can be a delicate and/or difficult procedure.

The embodiment of the present invention shown in FIGS. 6 and 7 addresses the difficulties mentioned above in advancing a shorter-guide-wire-lumen catheter over a guide wire. The shorter-guide-wire-lumen catheter 90 has a manifold (not shown) located at the proximal end of the elongate shaft 97. The manifold includes a port communicating with an inflation lumen that extends through the shaft 97 and that communicates with the balloon. The inflation lumen is used to convey fluid for the inflation of the balloon to dilate a stenosed artery in a conventional manner.

The guide wire and distal portion of the catheter are positioned inside of the guide catheter 40. As in the previous embodiment, the Y-adapter 50 is connected to a proximal end of the guide catheter 40. The hemostatic valve 60 connects to the Y-adapter 50 and allows for sealing the port 54 of the Y-adapter 50 around the dilation catheter 90. As in the previous embodiment, the O-ring 70 is located in the hemostatic valve 60 to seal the proximal end of the guide catheter 40 on the catheter shaft 97 to prevent back bleeding.

With a catheter of the type that has a shorter-guide-wire-lumen, the guide wire 92 can also extend out of the port 54 of the Y-adapter 50 through the hemostatic seal valve 60. In this embodiment, the sleeve 80 is located on the catheter shaft 97. As in the previous embodiment, the sleeve 80 is slidable along the shaft 97 but is close-fitting on the shaft 97 to reduce or prevent bleeding between the inside of the sleeve 80 and the shaft 97. In this embodiment, the guide wire 92 occupies a position outside of the sleeve 80. The dilation catheter 90 with sleeve 80 can be operated in a similar manner to the previous embodiment. The hemostatic valve 60 can be tightened down on the sleeve 80 to reduce or prevent back bleeding while allowing the catheter shaft 97 to be advanced relative to the sleeve 80 (and guide catheter 40). As in the previous embodiment, the sleeve 80 facilitates adjustment of the hemostatic valve 60 to allow for dilation catheter movement relative to the guide catheter 40 while reducing or preventing back bleeding through the hemostatic valve 60.

In addition, in this embodiment, the sleeve 80 provides an additional function. In this embodiment, the guide wire 92 occupies a position between the O-ring 70 and the sleeve 80. Thus, the guide wire 92 can be fixed in position relative to the guide catheter 40 by tightening of the O-ring 70 while yet allowing for advancement of the dilation catheter 90 over and with respect to the guide wire 92 for positioning in the arterial site. Thus, with the present embodiment, inadvertent jostling of the guide wire as the catheter 90 is advanced over it can be reduced, especially when the guide wire 92 is already in position in the arterial site such as when the guide wire is installed first or when a second catheter is being advanced over the guide wire after an exchange.

The sleeve 80 in this embodiment may be similar or identical to the sleeve described above for use with the fixed-wire type dilation catheter 10. In this embodiment, the sleeve 80 is located on the shaft 97 between the manifold (or the strain relied) and the proximal guide wire opening 98. The sleeve 80 is readily movable along the shaft 97, but is close-fitting to thereby reduce or prevent leakage of blood between the elongate shaft 97 and the sleeve 80.

Referring to FIG. 7, to facilitate location of the guide wire adjacent to the shaft 97, a slot 120 may be formed in the hub portion 88. The slot 120 is sized to accommodate location of the guide wire 92 therein. In a preferred embodiment, the bottom of the slot 120 is inclined to direct the guide wire proximally at an angle away from the catheter shaft 97 to facilitate handling and use.

OTHER ALTERNATIVE EMBODIMENTS

Although the sleeve 80 is preferably non-removable and incorporated on the dilation catheter during the manufacture thereof, in alternative embodiments, the sleeve 80 may be removable from the catheter shaft. To provide for a removable sleeve, the sleeve 80 may be slotted or scieved along its length to allow for placement on the catheter shaft. In such an embodiment, the removable sleeve may be provided with the catheter either separately or already mounted thereon but removable therefrom. Alternatively, a removable sleeve may be provided as a separate component apart from a specific catheter but sized and adapted for use with catheters of certain sizes and mountable thereon. In still further alternative embodiments, the sleeve 80 may be removable from the catheter shaft either by sliding distally over the balloon portion, or by providing a removable manifold on the catheter and sliding the sleeve proximally after removing the manifold.

Further, although the embodiments discussed above are described for use with a conventional hemostatic valve in a Y-adapter connected to a conventional guide catheter, it is intended that the present invention could be used with any type of blood sealing device associated with an introducer or sheath device used for access into a blood vessel. For example, other types of blood sealing valves are used that do not incorporate an adjustable O-ring. Such other types of valves include self-adjusting types or those which have a collapsible membrane that conforms to the device, such as the catheter, guide wire, etc., extending therethrough. The sleeve of the above described embodiments of the present invention could be used with such types of sealing valves to provide for improved, unimpeded shaft movement while reducing blood loss.

In further alternatives, although the embodiments discussed above are described for use with a conventional hemostatic valve in a Y-adapter connected to a conventional guide catheter, it is intended that the present invention could be used with any type of adapter or manifold, other than a conventional Y-adapter. For example, other adapters have more or fewer than two ports, or may be formed of additional pieces of tubing.

Although it has been described above that the sleeve 80 is constructed to provide for unimpeded shaft movement when the hemostatic valve of the Y-adapter is tightened and the O-ring sealed on the sleeve 80, in a further preferred alternative embodiment, the sleeve may be provided such that the catheter shaft may be fixed in position with respect to the hemostatic valve (and therefore the guide catheter) by sufficient, additional adjustment of the hemostatic valve. In such an embodiment, the sleeve would be provided of a material and in a size so that when the O-ring is intially clamped down on the sleeve, unimpeded catheter shaft movement is provided, but when further additional pressure is applied by tightening of the hemostatic valve, the sleeve collapses or deforms onto the catheter shaft to fix it in position relative to the Y-adapter. In a preferred embodiment, the sleeve would be resilient so that the physician could repeatedly fix, and then release the catheter shaft, as necessary. Further, the sleeve would also preferably be provided such that the additional pressure required to fix the catheter shaft is sufficiently greater than the initial pressure required to prevent back bleeding around the shaft in order to provide for a well-defined range to facilitate adjustment and use by the physician.

In a yet further alternative embodiment, the present invention may be adapted for use with a catheter of the over-the-wire type. An over-the-wire catheter has a separate guide wire lumen extending therethrough. A sleeve 80 such as described above may be incorporated onto an over-the-wire catheter to reduce or prevent back bleeding around the shaft of such a catheter and would be particularly useful for use with an over-the-wire catheter having a small diameter shaft.

It is intended that the foregoing detailed description be regarded as illustrative rather than limiting and that it is understood that the following claims including all equivalents are intended to define the scope of the invention.

I claim:

1. A method of performing an intravascular procedure with an guide wire and intravascular catheter having an elongate shaft, an implement located at a distal portion thereof, and a close-fitting sleeve located around the shaft and movable therealong, and further in which the intravascular catheter has a lumen shorter than a length of the catheter and having a proximal opening located at the distal portion of the elongate shaft communicating with the shorter lumen, and further in which said sleeve is located around the elongate shaft proximally of the proximal opening, the method comprising the steps of:

advancing the guide wire intravascularly;

positioning the intravascular catheter over the guide wire in an introducer device having a hemostatic valve located at a proximal end thereof;

positioning the close fitting sleeve at the hemostatic valve;

positioning a proximal portion of the guide wire between the sleeve and the hemostatic valve;

tightening the hemostatic valve on the sleeve to form a seal between the sleeve, the guide wire and the hemostatic valve; and advancing the intravascular catheter along the guide wire.

2. The method of claim 1 further comprising the step of:

positioning the guide wire in a slot located in a hub located on a sleeve.

3. The method of claim 2 further comprising the step of:

withdrawing the catheter after performing the intravascular procedure by moving the catheter in a proximal direction while the hemostatic valve is sealingly tightened on the sleeve and the guide wire.

4. The method of claim 1 in which the introducer device is a guide catheter.

5. The method of claim 1 in which the implement is a dilation balloon and the method further comprises the step of:

performing an intravascular dilation with the dilation balloon.

6. The method of claim 1 in which the proximal opening communicating with the lumen of the intravascular catheter is located proximally of the implement.

7. The method of claim 1 further comprising:

after the step of tightening the hemostatic valve on the sleeve to form a seal between the sleeve, the guide wire and the hemostatic valve, then applying additional pressure to further tighten the hemostatic valve on the sleeve to fix the position of the catheter relative to the hemostatic valve and the sleeve.

8. The method of claim 7 in which the additional pressure to fix the position of the catheter relative to the hemostatic valve and sleeve is sufficiently greater than pressure required to form a seal between the catheter, the sleeve and the hemostatic valve to establish a range of pressures at which only a seal is provided between the catheter, the sleeve, and the hemostatic valve.

9. The method of claim 1 in which the sleeve is resilient in order that the step of tightening the hemostatic valve on the sleeve may be performed multiple times.

10. The method of claim 1 further comprising:

removing the sleeve from the shaft of the catheter.

11. The method of claim 10 in which the sleeve is removed from the catheter shaft through a slit formed along a side of the sleeve.

12. The method of claim 1 in which the sleeve is provided as a separate component, and the method further comprises:

positioning the sleeve on the elongate shaft of the catheter.

* * * * *